US007016506B2

(12) United States Patent
Chiara

(10) Patent No.: US 7,016,506 B2
(45) Date of Patent: Mar. 21, 2006

(54) MODULAR ACTIVE NOISE AIR FILTER SPEAKER AND MICROPHONE ASSEMBLY

(75) Inventor: Brian Chiara, Commerce Township, MI (US)

(73) Assignee: Siemens VDO Automotive Inc., Chatham (CA)

( * ) Notice: Subject to any disclaimer, the term of this patent is extended or adjusted under 35 U.S.C. 154(b) by 158 days.

(21) Appl. No.: 10/255,117

(22) Filed: Sep. 25, 2002

(65) Prior Publication Data

US 2003/0059058 A1 Mar. 27, 2003

Related U.S. Application Data

(60) Provisional application No. 60/324,699, filed on Sep. 25, 2001.

(51) Int. Cl.
*A61F 11/06* (2006.01)

(52) U.S. Cl. .................................................... 381/71.4

(58) Field of Classification Search ............... 381/71.4, 381/715, 71.1, 86, 96
See application file for complete search history.

(56) References Cited

U.S. PATENT DOCUMENTS

| | | | | |
|---|---|---|---|---|
| 3,936,606 A | | 2/1976 | Wanke | |
| 4,410,065 A | | 10/1983 | Harvey | |
| 4,665,549 A | | 5/1987 | Eriksson et al. | |
| 4,832,262 A | | 5/1989 | Robertson | |
| 4,876,722 A | | 10/1989 | Dekker et al. | |
| 4,896,718 A | | 1/1990 | Trin | |
| 4,947,434 A | | 8/1990 | Ito | |
| 5,170,019 A | | 12/1992 | Lee | |
| 5,197,426 A | | 3/1993 | Frangesch et al. | |
| 5,229,556 A | | 7/1993 | Geddes | |
| 5,271,120 A | | 12/1993 | Eustache et al. | |
| 5,319,165 A | | 6/1994 | Geddes | |
| 5,336,856 A | | 8/1994 | Krider et al. | |
| 5,426,703 A | | 6/1995 | Hannabe et al. | |
| 5,426,705 A | | 6/1995 | Yokota et al. | |
| 5,432,857 A | | 7/1995 | Geddes | |
| 5,446,249 A | | 8/1995 | Goodman et al. | |
| 5,446,790 A | | 8/1995 | Tanaka et al. | |
| 5,457,749 A | | 10/1995 | Cain et al. | |
| 5,466,899 A | | 11/1995 | Geisenberger | |
| 5,499,423 A | * | 3/1996 | Joo et al. | 15/319 |
| 5,513,266 A | | 4/1996 | Zuroski | |
| 5,541,373 A | | 7/1996 | Cheng | |
| 5,550,334 A | | 8/1996 | Langley | |
| 5,587,563 A | | 12/1996 | Yazici et al. | |
| 5,647,314 A | | 7/1997 | Matsumura et al. | |
| 5,693,918 A | | 12/1997 | Bremigan et al. | |
| 5,828,759 A | | 10/1998 | Everingham | |

(Continued)

FOREIGN PATENT DOCUMENTS

DE 196 10 292 A1 9/1996

(Continued)

OTHER PUBLICATIONS

"Acoustic Plant for Active Induction Noise Control"; Research Disclosure, Kenneth Mason Publications, Hampshire, GB, No. 316, Aug. 1, 1990.

(Continued)

*Primary Examiner*—Laura A. Grier

(57) ABSTRACT

An air induction system comprises an air induction body and air filter to provide filtered air to a vehicle engine. A microphone is disposed within the air filter. A control unit may receive signals from the microphone. The control unit may further control a speaker, which produces a noise canceling sound to thereby reduce engine noise associated with the air induction system.

23 Claims, 1 Drawing Sheet

U.S. PATENT DOCUMENTS

| | | | | |
|---|---|---|---|---|
| 5,913,295 | A | | 6/1999 | Sadr et al. |
| 5,946,763 | A | | 9/1999 | Egner-Walter et al. |
| 5,954,847 | A | * | 9/1999 | Shively et al. ............. 55/385.3 |
| 6,009,705 | A | | 1/2000 | Arnott et al. |
| 6,084,971 | A | * | 7/2000 | McLean .................... 381/71.5 |
| 6,160,892 | A | * | 12/2000 | Ver ........................... 381/71.5 |
| 6,213,077 | B1 | | 4/2001 | Horii |

FOREIGN PATENT DOCUMENTS

| | | | |
|---|---|---|---|
| EP | 0 884 471 | A2 | 12/1998 |
| EP | 0 884 471 | A3 | 12/1998 |
| EP | 0 952 025 | A2 | 10/1999 |
| EP | 0 992 976 | A2 | 4/2000 |
| GB | 2 279 778 | A | 1/1995 |
| JP | 10103173 | | 4/1998 |
| JP | 01238427 | | 9/1998 |

OTHER PUBLICATIONS

International Search Report, mailed Jan. 25, 2002.

U.S. Appl. No. 09/931,394, filed Aug. 16, 2001, entitled "Environmentally Robust Noise Attenuation System".

* cited by examiner

MODULAR ACTIVE NOISE AIR FILTER SPEAKER AND MICROPHONE ASSEMBLY

This application claims priority to U.S. Provisional Patent Application Ser. No. 60/324,699 filed on Sep. 25, 2001.

BACKGROUND OF THE INVENTION

This invention relates to a system of noise attenuation around an air induction assembly.

Manufacturers have employed active and passive methods to reduce engine noise within a passenger compartment of a vehicle. Such noise frequently emanates from the engine, travels through the air induction system and emanates out of the mouth of the air intake into the passenger compartment. Efforts have been made to reduce the amount of engine noise traveling through the air induction system. These efforts include the use of both passive devices, such as expansion chambers and Helmholtz resonators, and active devices involving anti-noise generators.

Active systems use a speaker to create a canceling sound that attenuates engine noise. The sound created is out of phase with the engine noise and combines with this noise to result in its reduction. Generally, this sound is generated in proximity to the mouth of the air induction system. In one such system, a control unit, such as a digital signal processor, obtains data from the vehicle engine, creates a predictive model of engine noise, and then generates the appropriate canceling signal based on the results of this model. This signal is then transmitted to the speaker, which transforms this signal into a canceling sound. Because the control unit may not perfectly model engine noise, an error microphone is placed in proximity to the mouth of the air induction system to determine if engine noise need be further attenuated.

The microphone for such a system is typically mounted to the speaker housing and located at the mouth of the air intake. This location, however, subjects this sensitive device to the hostile environment around the air intake mouth, exposing the microphone to road conditions, debris, and foul weather. As a consequence, the microphone may be damaged during vehicle operation resulting in the malfunctioning of the noise attenuation system.

In addition, the noise attenuation system is frequently made of a number of separate components, which require assembly on the production line of the vehicle. These components include the microphone, the speaker and speaker volume, and air filter. The separate assembly of these components into the air induction system accordingly results in reduced productivity.

A need therefore exists to provide a more robust and simplified noise attenuation device for an air induction system.

SUMMARY OF THE INVENTION

Like existing noise attenuating devices for air induction systems, the present invention has an air induction body to receive air for a vehicle engine. An air filter serves to filter air that passes through the air induction body. In contrast to existing systems, however, the invention places a microphone of a noise attenuation device within the air filter, thereby protecting the microphone from a variety of hostile conditions and greatly simplifying assembly of the noise attenuation device into the air induction system.

The invention further employs a speaker and speaker chamber. A control unit controls output from the speaker so as to create a noise attenuating sound. The speaker directs this sound towards the engine, the source of noise, through the air filter and the air induction body to thereby attenuate engine noise. In addition, the control unit may receive a signal from the microphone. This signal may represent noise not cancelled by the speaker. Based on the received signals, the control unit may adjust the output of the speaker to further minimize remaining noise.

The invention further includes a novel air filter unit. As mentioned previously, a microphone is placed within the air filter. In addition, a speaker may be mounted to the air filter, which may be radial in shape. The speaker may also be mounted to the speaker chamber, which is itself mounted to the air filter. Accordingly, the speaker and speaker chamber maybe attached to one end of the air filter. The other end may then be attached to the air induction body. The microphone, speaker, speaker chamber and air filter thus form a single unit that may be easily installed into the air induction body.

In this way, the inventive air induction system and air filter unit protects the microphone of a noise attenuation device from debris, hostile weather, and other elements that may damage the microphone. The air filter unit is modular in design and may be quickly installed into the air induction system without separate assembly of the parts on a production line. The invention accomplishes these objectives without significant cost or expense.

BRIEF DESCRIPTION OF THE DRAWINGS

The various features and advantages of this invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
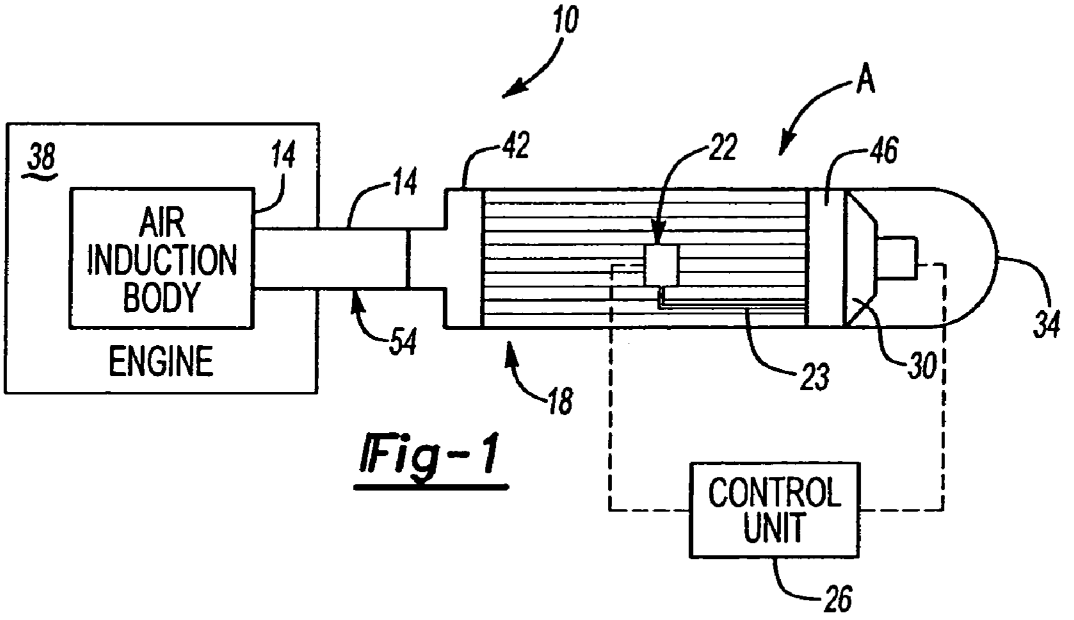
FIG. 1 illustrates the inventive air induction system, including air filter, microphone and speaker.

FIG. 1 illustrates inventive air induction system 10, which may comprise air induction body 14, air filter 18, microphone 22, control unit 26, speaker 30, and speaker volume 34. Air is received through air filter 18, such as along arrow A. Air induction body 14 then provides air to engine 38 as known while air filter 18 ensures that air received by air induction body 14 and transmitted to engine 38 is cleansed of debris and particulates. While air may travel through air induction body 14 towards engine 38, noise from engine 38 may also travel through the same body 14 and eventually to a passenger compartment (not shown). To reduce this noise, control unit 26 creates a noise attenuating sound through speaker 30 and speaker volume 34. This noise attenuating sound is out of phase with noise emanating from engine 38 resulting in the reduction of this noise. As known, noise not attenuated by speaker 30 is picked up by microphone 22, an error microphone, which sends a signal to control unit 26. Feedback from microphone 22 permits control unit 26 to adjust sound from speaker 30 to further attenuate engine noise.

In contrast to existing noise attenuation devices and air induction systems, air induction system 10 protects microphone 22 by disposing microphone 22 within air filter 18 (here shown as a radial air filter). Microphone 22 is essentially jacketed by air filter 18. Further, microphone 22 is spaced between speaker 46 and engine 38 to additionally protect microphone 22 from the hostile elements around the air intake.

Figure 2:
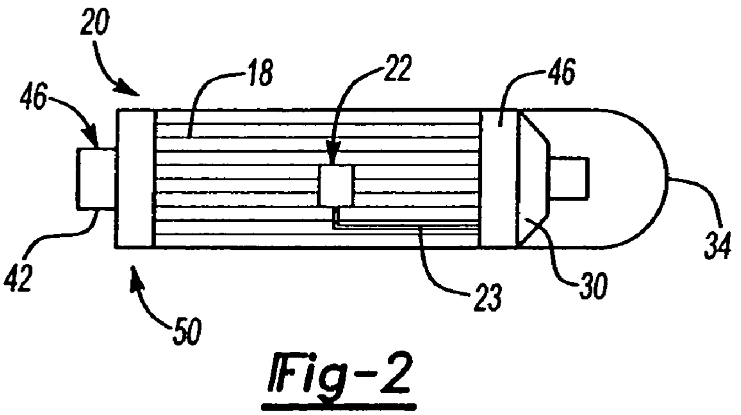
FIG. 2 illustrates the inventive air filter unit, including air filter, speaker and microphone.

FIG. 2 illustrates air filter unit 20 employed with air induction system 10 as illustrated in FIG. 1. As shown, microphone 22 is disposed within air filter 18. Microphone 22 may be placed 50 to 100 mm away from speaker 30, which also provides support for microphone 22 as shown through support arm 23. Speaker 30 has speaker chamber 34, which permits speaker 30 to produce a range of noise attenuating sounds in conjunction with control unit 26 as known. Speaker volume 34, such as a speaker chamber, is mounted to air filter 18 through connector 46. Air filter unit 20 thereby forms a single body supporting air filter 18, microphone 22, speaker 30 and speaker volume 34. As shown, connector 42 is also attached to air filter 18 and may comprise first portion 46 and second portion 50. First portion 46 maybe cylindrical in shape and sized to be inserted and secured by sleeve 54 of air induction body 14. In this way, air filter unit 20 may be quickly and easily installed into air induction body 14 during vehicle production.

The aforementioned description is exemplary rather that limiting. Many modifications and variations of the present invention are possible in light of the above teachings. The preferred embodiments of this invention have been disclosed. However, one of ordinary skill in the art would recognize that certain modifications would come within the scope of this invention. Hence, within the scope of the appended claims, the invention may be practiced otherwise than as specifically described. For this reason the following claims should be studied to determine the true scope and content of this invention.

What is claimed is:

1. An air induction system for a motorized vehicle, comprising:

a vehicular air induction body for receiving air;

an air filter in communication with said vehicular air induction body, said air filter for directing air to a vehicle engine;

a microphone disposed within said air filter, said air filter physically protecting the microphone from an environment; and a control unit in communication with said microphone.

2. The air induction system of claim 1 including a speaker in communication with said vehicular air induction body.

3. The air induction system of claim 2 wherein said speaker is in communication with said control unit.

4. The air induction system of claim 2 including a speaker volume in communication with said speaker.

5. The air induction system of claim 2 wherein said speaker is in communication with an engine.

6. The air induction system of claim 5 wherein said microphone is spaced between said engine and said speaker.

7. The air induction system of claim 2 wherein said microphone and said speaker are operatively mounted to said air filter to form an air filter unit.

8. The air induction system of claim 7, including a connector for selectively engaging said air filter unit to said vehicular air induction body.

9. The air induction system of claim 7, wherein said air filter unit forms a selectively separable component from said vehicular air induction body.

10. The air induction system of claim 2, wherein said speaker faces said vehicular air induction body.

11. The air induction system of claim 2, wherein said speaker faces said air filter in a direction in which air is received by said air filter.

12. An air induction system for a motorized vehicle, comprising:

a vehicular air induction body for receiving air;

an air filter in communication with said vehicular air induction body;

a microphone disposed within said air filter, said air filter physically protecting the microphone from an environment;

a control unit in combination with said microphone; and wherein said air filter comprises a radial air filter.

13. An air induction system, comprising:

an air induction body for receiving air;

an air filter in communication with said air induction body, said air induction body arranged to receive air from said air filter;

a microphone disposed within said air filter, said air filter physically protecting the microphone from an environment;

a control unit in communication with said microphone; and a speaker controlled by said control unit and in communication with said air induction body wherein said microphone is spaced between a vehicle engine and said speaker.

14. The air induction system of claim 13 including a speaker volume in communication with said speaker.

15. The air induction system of claim 13 wherein said microphone and said speaker are operatively mounted to said air filter.

16. The air induction system of claim 13 wherein said air filter comprises a radial air filter.

17. An air filter unit for an automobile, comprising:

an automotive air filter;

a microphone disposed within said automotive air filter, said air filter physically protecting the microphone from an environment; and a speaker mounted to said automotive air filter; and wherein said automotive air filter comprises a radial filter.

18. The air filter unit of claim 17 including a speaker volume in communication with said speaker.

19. The air filter unit of claim 18 wherein said speaker is mounted to said speaker volume.

20. The air filter unit of claim 19 wherein said speaker volume is mounted to said automotive air filter.

21. The air filter unit of claim 17 including a control unit in communication with said microphone and said speaker.

22. The air filter unit of claim 21 wherein said control unit controls output of said speaker to create a noise attenuating sound.

23. The air filter unit of claim 17 including an air induction body in communication with said automotive air filter and said speaker.

* * * * *